US011304997B2

(12) United States Patent
Miyakawa et al.

(10) Patent No.: US 11,304,997 B2
(45) Date of Patent: Apr. 19, 2022

(54) HSP70-DERIVED PEPTIDE, PHARMACEUTICAL COMPOSITION FOR TREATING OR PREVENTING CANCER USING SAME, IMMUNITY INDUCER, AND METHOD FOR PRODUCING ANTIGEN-PRESENTING CELL

(71) Applicant: CYTLIMIC INC., Tokyo (JP)

(72) Inventors: Tomoya Miyakawa, Tokyo (JP); Masaaki Oka, Yamaguchi (JP); Shoichi Hazama, Yamaguchi (JP); Koji Tamada, Yamaguchi (JP); Keiko Udaka, Kochi (JP)

(73) Assignee: CYTLIMIC INC., Tokyo (JP)

( * ) Notice: Subject to any disclaimer, the term of this patent is extended or adjusted under 35 U.S.C. 154(b) by 136 days.

(21) Appl. No.: 16/715,758

(22) Filed: Dec. 16, 2019

(65) Prior Publication Data

US 2020/0121772 A1 Apr. 23, 2020

Related U.S. Application Data

(62) Division of application No. 15/516,918, filed as application No. PCT/JP2015/078504 on Oct. 7, 2015, now Pat. No. 10,537,626.

(30) Foreign Application Priority Data

Oct. 7, 2014 (JP) ................................ 2014-206730

(51) Int. Cl.
| A61K 39/00 | (2006.01) |
| C07K 7/06 | (2006.01) |
| C12N 15/09 | (2006.01) |
| A61K 38/00 | (2006.01) |
| A61K 47/50 | (2017.01) |

(52) U.S. Cl.
CPC ...... *A61K 39/001176* (2018.08); *A61K 38/00* (2013.01); *A61K 39/00* (2013.01); *A61K 39/0011* (2013.01); *A61K 47/50* (2017.08); *C07K 7/06* (2013.01); *C12N 15/09* (2013.01); *A61K 2039/545* (2013.01)

(58) Field of Classification Search
CPC ............ A61K 39/001176; A61K 38/00; A61K 39/00; A61K 39/0011; A61K 47/50; A61K 2039/545; C07K 7/06; A61P 35/00
See application file for complete search history.

(56) References Cited

U.S. PATENT DOCUMENTS

| 5,196,523 | A | 3/1993 | Lee |
| 2002/0192195 | A1 | 12/2002 | Triebel |
| 2003/0171280 | A1 | 9/2003 | Soderstrom |
| 2004/0063173 | A1 | 4/2004 | Multhoff |
| 2007/0081991 | A1 | 4/2007 | Soderstrom |
| 2007/0087009 | A1 | 4/2007 | Burdin et al. |
| 2009/0035330 | A1 | 2/2009 | Dewerchin |
| 2009/0123460 | A1 | 5/2009 | Noelle et al. |
| 2009/0155308 | A1 | 6/2009 | Moon et al. |
| 2009/0239806 | A1 | 9/2009 | Nishimura et al. |
| 2010/0015101 | A1 | 1/2010 | Sato et al. |
| 2010/0028373 | A1 | 2/2010 | Fujioka et al. |
| 2011/0028403 | A1 | 2/2011 | Le Poole et al. |
| 2013/0217122 | A1 | 8/2013 | Kaplan |
| 2015/0023992 | A1 | 1/2015 | Sette et al. |
| 2015/0285806 | A1 | 10/2015 | Ohtomo et al. |
| 2018/0071362 | A1 | 3/2018 | Miyakawa et al. |

FOREIGN PATENT DOCUMENTS

| CA | 2963909 A1 | 4/2016 |
| CN | 101568550 A | 10/2009 |
| EP | 1002108 | 5/2000 |
| EP | 1750707 | 2/2007 |
| EP | 2214705 | 8/2010 |
| EP | 2214705 B1 | 8/2010 |
| EP | 2572715 A1 | 3/2013 |
| JP | 08-151396 A | 6/1996 |
| JP | 2001-510806 A | 8/2001 |
| JP | 2006-512391 A | 4/2006 |
| JP | 2007-514725 A | 6/2007 |
| JP | 2008-540625 A | 11/2008 |
| JP | 2010-538655 A | 12/2010 |
| JP | 2011-506309 A | 3/2011 |
| RU | 2333767 C2 | 10/2007 |
| RU | 2709015 C2 | 4/2019 |
| WO | WO 99/04810 A2 | 2/1999 |
| WO | WO 2004/018667 A1 | 3/2004 |
| WO | WO 2005/060966 A1 | 7/2005 |
| WO | WO 2007/018199 A1 | 2/2007 |
| WO | WO 2007/119515 A1 | 10/2007 |
| WO | WO 2008/106491 A2 | 9/2008 |
| WO | WO-2009/008719 A2 | 1/2009 |
| WO | WO 2009/072767 A2 | 6/2009 |
| WO | WO 2011/044246 A1 | 4/2011 |
| WO | WO 2013/119863 A1 | 8/2013 |

(Continued)

OTHER PUBLICATIONS

O'Beirne et al., "Generation of functional CD8 T Cells by Human dendritic cells expressing glypican-3 epitopes," Journal of Experimental & Clinical Cancer Research, 2010, 29:48, 11 pages.

Office Action dated Sep. 1, 2020 in Chinese Application No. 201680014548.9, with English translation.

Sun et al., "Immune activity evaluation of GPC3 peptides recognized by HLA-A11 restricted T lymphocytes in hepatocellular carcinoma patients," Beijing Medical Journal, Dec. 31, 2014, 36(9):752-755.

(Continued)

*Primary Examiner* — Lei Yao
(74) *Attorney, Agent, or Firm* — Foley & Lardner LLP

(57) ABSTRACT

The present invention provides a peptide containing 8 or more consecutive amino acid residues in an amino acid sequence of any of SEQ ID NOS: 1 to 15 and consisting of 11 or less amino acid residues.

5 Claims, 6 Drawing Sheets

Specification includes a Sequence Listing.

(56) References Cited

FOREIGN PATENT DOCUMENTS

| WO | WO 2013/143026 A1 | 10/2013 |
|---|---|---|
| WO | WO-2014/097648 A1 | 6/2014 |
| WO | WO 2014/134355 A1 | 9/2014 |
| WO | WO 2015/168379 A2 | 11/2015 |
| WO | WO 2016/056596 A1 | 4/2016 |
| WO | WO 2016/143816 A1 | 9/2016 |
| WO | WO 2016/163489 A1 | 10/2016 |

OTHER PUBLICATIONS

Tada et al., "Analysis of cytotoxic T lymphocytes from a patient with hepatocellular carcinoma who showed a clinical response to vaccination with a glypican-3-derived peptide," International Journal of Oncology, Dec. 31, 2013, 43:1019-1026.
Office Action dated Jun. 22, 2021, in CN 201580054234.7, with English translation.
Shang, Wei, Ed., Clinical Bio-Immunotherapy for Tumors, Tianjin Science and Technology Press, Jan. 31, 2006, 284-285, with English translation.
Office Action dated Mar. 17, 2020, in AU 2016244570.
Belikov, V.G., Vysshaya Shkola, 1993, 43-47.
Jiang et al., "Expression significance of HLA-DR antigen and heat shock protein 70 in hepatocellular carcinoma," World Chinese Journal of Digestology, Oct. 15, 2001, 9(10):1139-1142, with English abstract.
Mashkovsky, M.D., Navaya Volna, 2001, 1(14):11.
Office Action dated May 19, 2020, in RU 2019113989, with English translation.
Office Action dated May 28, 2020, in CN 201580054234.7, with English translation.
Sabbatini et al., "Phase I Trial of Overlapping Long Peptides from a Tumor Self-Antigen and Poly-ICLC Shows Rapid Induction of Integrated Immune Response in Ovarian Cancer Patients," Clinical Cancer Research, 2012, 18(23):6497-6508.
Zhu et al., "Toll like receptor-3 ligand poly-ICLC promotes the efficacy of peripheral vaccinations with tumor antigen-derived peptide epitopes in murine CNS tumor models," Journal of Translational Medicine, Feb. 12, 2007, 5(10):15 pages.
Office Action dated Apr. 4, 2021 in CN 201680014548.9.
Allowance dated Apr. 7, 2021 in CN 201680014548.9.
AdipoGen™ Safety Data Sheet, "LAG-3 (mouse):Fc mMouse) (rec)," May 5, 2011, 3 pages.
American Cancer Society, "Non-specific cancer immunotherapies and adjuvants," Aug. 8, 2016, 4 pages.
Ammi et al., "Poly(I:C) as cancer vaccine adjuvant: Knocking on the door of medical breakthroughs," Pharmacology & Therapeutics, 2015, vol. 146, pp. 120-131.
Brignone et al., "A Soluble Form of Lymphocyte Activation Gene-3 (IMP321) Induces Activation of a Large Range of Human Effector Cytotoxic Cells," The Journal of Immunology, 2007, 179:4202-4211.
Ebner et al., "Identification of Multiple T Cell Epitopes on Bet v I, the Major Birch Pollen Allergen, Using Specific T Cell Clones and Overlapping Peptides," The Journal of Immunology, Feb. 1, 1993, 150(3):1047-1054.
Faure et al., "Inducible Hsp70 as Target of Anticancer Immunotherapy: Identification of HLA-A*0201-Restricted Epitopes," Int. J. Cancer, Mar. 1, 2004, 108(6):863-870.
Fougeray et al., "A soluble LAG-3 protein as an immunopotentiator for therapeutic vaccines: Preclinical evaluation of IMP321," Vaccine, Jun. 29, 2006, 24(26):5426-5433.
Fransen et al., "Local immunomodulation for cancer therapy," OncoImmunology, Nov. 1, 2013, 2(11):e26493, 3 pages.
Galluzzi et al., "Trial Watch: Experimental Toll-like receptor agonists for cancer therapy," OncoImmunology, Aug. 1, 2012, 1(5):699-739.
Goldberg et al., "LAG-3 in Cancer Immunotherapy," Curr. Top. Microbiol. Immunol., Jan. 1, 2011, 344:269-278.
Guha, Malini, "Anticancer TLR agonists on the ropes," Nature Reviews Drug Discovery, Jul. 2012, 11(7):503-505.
Harig et al., "Induction of cytotoxic T-cell responses against immunoglobulin V region-derived peptides modified at human leukocyte antigen-A2 binding residues," Blood, Nov. 15, 2001, 98(10):2999-3005.
International Search Report dated Jun. 14, 2016, in PCT/JP2016/057356.
International Search Report dated Jun. 27, 2017, in PCT/JP2017/015227.
International Search Report dated Jun. 28, 2016, in PCT/JP2016/061463.
International Search Report dated Nov. 24, 2015, in PCT/JP2015/078504.
Iwama et al., "Identification of an $H2-K^b$ or $H2-D^b$ restricted and glypican-3-derived cytotoxic T-lymphocyte epitope peptide," International Journal of Oncology, Jan. 23, 2013, 42(3):831-838.
Kano et al., "Combined adjuvants of poly(I:C) plus LAG-3-lg improve antitumor effects of tumor-specific T cells, preventing their exhaustion," Cancer Sci., Apr. 15, 2016, 107(4):398-406.
Komori et al., "Identification of HLA-A2- or HLA-A24-Restricted CTL Epitopes Possibly Useful for Glypican-3-Specific Immunotherapy of Hepatocellular Carcinoma," Clin. Cancer Res., May 1, 2006, 12(9):2689-2697.
Nakatsura et al., "Mouse Homologue of a Novel Human Oncofetal Antigen, Glypican-3, Evokes T-Cell-Mediated Tumor Rejection without Autoimmune Reactions in Mice," Clinical Cancer Research, Dec. 15, 2004, 10(24):8630-8640.
Office Action dated Aug. 29, 2019, in RU 201735038, with English translation.
Office Action dated Jan. 28, 2019, in U.S. Appl. No. 15/556,694.
Office Action dated Jun. 17, 2019, in U.S. Appl. No. 15/564,604.
Office Action dated Oct. 17, 2017, in JP 2017-511073.
Office Action dated Oct. 17, 2019, in TW 104133022.
Office Action dated Sep. 20, 2019, in RU 2017134693, with English translation.
Office Action dated Mar. 23, 2018, in Russian Application No. RU 2017115719, with English translation.
Okochi et al., "Identification of HLA-A24-Restricted Epitopes with High Affinities to Hsp70 Using Peptide Arrays," Journal of Bioscience and Bioengineering, Mar. 2008, 105(3):198-203.
P.H.N. Celie et al., "Crystal structure of MHC CLass I HLA-A2.1 bound to HIV-1 envelope peptide env120-128," RCSB Protein Data Bank, 2010, https://www.rcsb.org/structure/2X4O, 6 pages.
Pan et al., "Interferon-γ is an autocrine mediator for dendritic cell maturation," Immunology Letters, May 26, 2004, 94(1-2):141-151.
Reed et al., "New horizons in adjuvants for vaccine development," Trends in Immunology, Dec. 6, 2008, 30(1):23-32.
Romano et al., "MART-1 peptide vaccination plus IMP321 (LAG-3Ig fusion protein) in patients receiving autologous PBMCs after lymphodepletion: results of a Phase I trial," Journal of Translational Medicine, Apr. 12, 2014, 12(97):1-12.
Sierro et al., "The CD4-like molecule LAG-3, biology and therapeutic applications," Expert Opin. On Ther. Targets, Jan. 2011, 15(1):91-101.
Supplemental European Search Report dated Jul. 11, 2018, in EP 15849707.3.
Supplementary European Search Report dated Nov. 16, 2018, in EP 16776655.9.
Supplementary Partial European Search Report dated Apr. 13, 2018, in EP 15849707.3.
Udaka et al., "An automated prediction of MHC class I-binding peptides based on positional scanning with peptide libraries," Immunogenetics, Jul. 8, 2000, 51(10):816-828.
Vacchelli et al., "Trial Watch: Toll-like receptor agonists for cancer therapy," OncoImmunology, Aug. 1, 2013, 2(8):e25238, 14 pages.
Wick et al., "Profound $CD8^+$ T cell immunity elicited by sequential daily immunization with exogenous antigen plus the TLR3 agonist poly(I:C)," Vaccine, 2011, 29:984-993.

(56) References Cited

OTHER PUBLICATIONS

Multhoff et al., "A 14-mer Hsp70 peptide stimulates natural killer (NK) cell activity," Cell Stress & Chaperones, Oct. 1, 2001, 6(4):337-344.
Partial European Search Report dated Oct. 29, 2021, in EP 21174944.5.

HSP70-DERIVED PEPTIDE, PHARMACEUTICAL COMPOSITION FOR TREATING OR PREVENTING CANCER USING SAME, IMMUNITY INDUCER, AND METHOD FOR PRODUCING ANTIGEN-PRESENTING CELL

CROSS-REFERENCE TO RELATED APPLICATIONS

This application is a Divisional of U.S. application Ser. No. 15/516,918, which is the U.S. National Stage of PCT/JP2015/078504, filed Oct. 7, 2015, which claims priority to JP 2014-206730, filed Oct. 7, 2014.

The instant application contains a Sequence Listing which has been submitted in ASCII format via EFS-WEB and is hereby incorporated by reference in its entirety. Said ASCII copy, created on Dec. 6, 2019, is named sequence.txt and is 9,091 bytes.

TECHNICAL FIELD

The present invention relates to an HSP70-derived peptide, more specifically an immunogenic peptide for presenting an antigen to a T cell via binding to a human leukocyte antigen, a pharmaceutical composition for treating or preventing cancer using the same, an immunity inducer, a method for producing an antigen-presenting cell, and the like.

BACKGROUND ART

Although it is considered that cancer cells always incidentally appear in a living body, it is hypothesized that the reaction by natural immunity normally occurs for elimination of a specific cancer antigen derived from cancer cells and that then a specific immune response is induced to cause the reaction of elimination of cancer cells by lymphocytes and other cells.

The recognition of a cancer cell-derived antigen requires the formation of a complex by a human leukocyte antigen (HLA) present on the cell surface and a lymphocyte. The HLA molecule as a major histocompatibility antigen is roughly divided into class I molecules (HLA types A, B, and C) and class II molecules (HLA types DP, DQ, and DR). The reaction of elimination of a cancer cell by a cytotoxic T cell (CTL) is induced by the specific recognition of a cancer antigen (CTL epitope) consisting of 8 to 11 amino acids which is presented on an HLA class I molecule on the cancer cell surface by a T cell antigen receptor (TCR) on the CTL.

The search for immunogenic peptides has been currently carried out with a view to their application to the treatment or prevention of various immune-related diseases; for example, Japanese Patent Laid-Open No. 08-151396 discloses that an oligopeptide consisting of a particular amino acid sequence has a HLA-binding capacity.

CITATION LIST

Patent Literature

Patent Literature 1: Japanese Patent Laid-Open No. 08-151396

SUMMARY OF INVENTION

Technical Problem

Many peptides having an HLA-binding capacity are known; however, there is further a need for peptides capable of being used for the treatment or prevention of various cancers. Since HLA gene is rich in polymorphism, there is also a need for multi-type immunogenic peptides each adaptable to a plurality of HLA types.

Solution to Problem

In view of the above-described circumstances, the present invention has an object of providing an immunogenic peptide capable of binding to an HLA class I molecule, particularly a peptide capable of inducing CTL, a pharmaceutical composition for treating or preventing cancer using the peptide, an immunity inducer, and a method for producing an antigen-presenting cell.

Specifically, the present invention includes the following inventions.

(1) A peptide comprising 8 or more consecutive amino acid residues in an amino acid sequence of any of SEQ ID NOS: 1 to 15 and consisting of 11 or less amino acid residues.

(2) The peptide according to (1), wherein in the amino acid sequence, 1 or several amino acids are substituted, inserted, deleted, or added, and the peptide has immunogenicity.

(3) The peptide according to (2), wherein in the amino acid sequence, the amino acid at position 2 is substituted by tyrosine, phenylalanine, methionine, tryptophan, valine, leucine, or glutamine, and/or the amino acid at the C-terminal is substituted by phenylalanine, leucine, isoleucine, tryptophan, methionine, or valine.

(4) A pharmaceutical composition for treating or preventing cancer, comprising the peptide according to any one of (1) to (3).

(5) The pharmaceutical composition according to (4), wherein the composition is in the form of a vaccine.

(6) The pharmaceutical composition according to (4) or (5), wherein the peptide can bind to one or more types of HLA molecules.

(7) An immunity inducer, comprising the peptide according to any one of (1) to (3).

(8) The immunity inducer according to (7), wherein the inducer is for inducing a cytotoxic T cell.

(9) The immunity inducer according to (7) or (8), wherein the peptide can bind to one or more types of HLA molecules.

(10) A method for producing an antigen-presenting cell having a CTL-inducing activity, comprising a step of contacting the peptide according to any one of (1) to (3) with an antigen-presenting cell in vitro.

Advantageous Effects of Invention

Attention has been given in recent years to immunotherapy as a method for treating cancer. The peptide of the present invention is strongly expected to have usefulness as a cancer vaccine because of its high HLA-binding capacity and also its high CTL-inducing capability. Its applications to various immunotherapies, particularly dendritic cell therapy, are also envisioned.

A heat shock protein (HSP) family is involved in varieties of cell functions, such as the folding, transport, modification, and protection of a protein, as a molecular chaperone (Zugel, U. and Kaufmann, S. H.: Role of heat-shock proteins in protection from and pathogenesis of infectious diseases., Clin. Microbiol. Rev. 12: 19-39, 1999). HSP is classified into 8 families: HSP110, HSP90, HSP70, HSP60, HSP40, HSP28, HSP27, and HSP25, based on the molecular size thereof. In addition, HSP has been known to be involved in cell death (apoptosis), and it is roughly divided into 2 groups: a group inhibiting apoptosis and a group inducing apoptosis.

HSP70 is a heat shock protein inhibiting apoptosis, and the high expression of HSP70 has been shown to be involved in the survival of cells under various situations, such as cell malignant transformation. In fact, it has been reported that HSP 70 protein from which the peptide of the present invention is derived is expressed in various cancers. (for example, 1. Yoshida et al., Anticancer Res. 2009 February; 29 (2): 539-44
2. Ciocca D R, Clark G M, Tandon A K, Fuqua S A, Welch W J and McGuire W L: Heat-shock protein hsp70 in patients with axillary lymph node-negative breast cancer: prognostic implications. J Natl Cancer Inst 85: 570-574, 1993
3. Kaur J and Ralhan R: Differential expression of 70-kDa heatshock protein in human oral tumorigenesis. Int J Cancer 63: 774-779, 1995
4. Park C S, Joo I S, Song S Y, Kim D S, Bae D S and Lee J H: An immunohistochemical analysis of heat-shock protein 70, p53, and estrogen receptor status in carcinoma of the uterine cervix. Gynecol Oncol 74: 53-60, 1999
5. Cornford P A, Dodson A R, Parsons K F, Desmond A D, Woolfenden A, Fordham M, Neoptolemos J P, Ke Y and Foster C: Heat-shock protein expression independently predicts clinical outcome in prostate cancer. Cancer Res 60: 7099-7105, 2000
6. Malusecka E, Zborek A, Krzyzowska-Gruca S and Krawczyk Z: Expression of heat-shock proteins HSP70 and HSP27 in primary non-small cell lung carcinomas. An immunohistochemical study. Anticancer Res 21: 1015-1021, 2001
7. Chuma M, Sakamoto M, Yamazaki K, Ohta T, Ohki M, Asaka M and Hirohashi S: Expression profiling in multistage hepatocarcinogenesis: identification of HSP70 as a molecular marker of early hepatocellular carcinoma. Hepatology 37: 198-207, 2003
8. Castle P E, Ashfaq R, Ansari F and Muller C Y: Immunohistochemical evaluation of heat-shock proteins in normal and preinvasive lesions of the cervix. Cancer Lett 229: 245-252, 2005
9. Kurahashi T, Miyake H, Hara I and Fujisawa M: Expression of major heat-shock proteins in prostate cancer: correlation with clinicopathological outcomes in patients undergoing radical prostatectomy. J Urol 177: 757-761, 2007.)

Among the peptides of the present invention, a particular peptide can bind to a plurality of HLA types. Thus, the peptide of the present invention enables, for example, the provision of a cancer vaccine and dendritic cell therapy covering an extremely wide range of cancer patients.

DESCRIPTION OF EMBODIMENTS

1. Immunogenic Peptide

Figure 1:
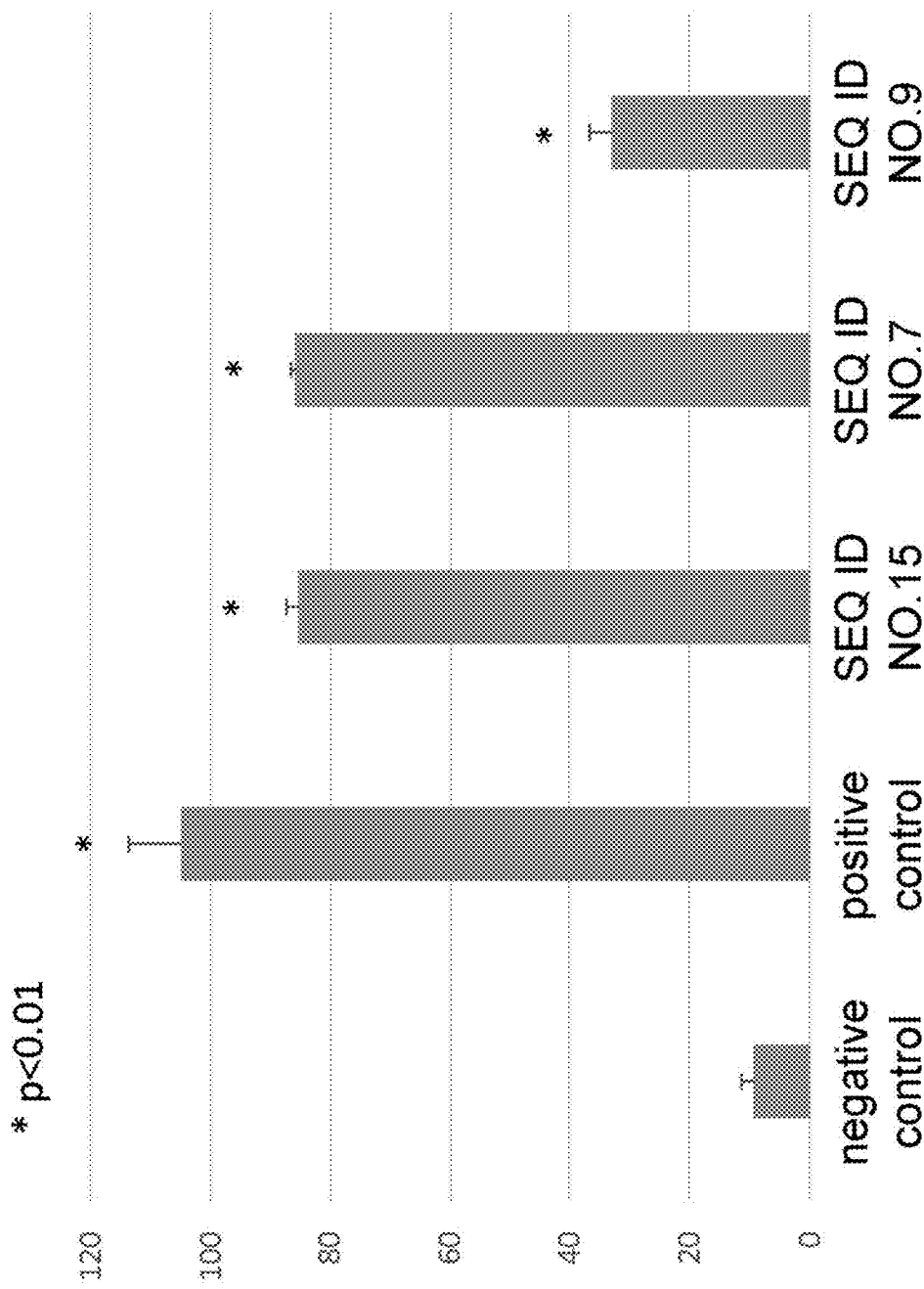
FIG. 1 is a graph showing the results of ELISPOT assay (the number of IFN-γ-producing cells) when samples derived from liver cancer patients (HLA type: 02:01/24:02) having received HSP70 dendritic cell therapy were stimulated with the peptide of SEQ ID NO: 7, 9, or 15.

The peptides according to the present invention are each a peptide comprising 8 or more consecutive amino acid residues in an amino acid sequence of any of SEQ ID NOS: 1 to 15 and consisting of 11 or less, preferably 10 or less, more preferably 9 or less amino acid residues in total. The peptide of the present invention may be a peptide consisting of an amino acid sequence of any of SEQ ID NOS: 1 to 15. The peptide of the present invention is derived from HSP70, which is one of the heat shock proteins. An amino acid sequence whose binding capacity to the HLA molecule is 3 or more in terms of a −log Kd value has been selected, and the binding capacity here was predicted by the hypothesis obtained using an active learning experiment method (Japanese Patent Laid-Open No. 08-151396) based on the amino acid sequence constituting HSP70.

The amino acid sequence constituting each peptide of the present invention and its HLA-binding prediction score are shown in Table 1 below.

TABLE 1

| Amino Acid Sequence | Position in | Binding Prediction Score | | |
|---|---|---|---|---|
| (SEQ ID NO:) | HSP70 | To A*24: 02 | To A*02: 01 | To A*02: 06 |
| GVPQIEVTF (SEQ ID NO: 1) | 470 | 6.8692 | 4.1663 | 4.1952 |
| TFDVSILTI (SEQ ID NO: 2) | 204 | 5.407 | 4.4626 | 4.2078 |

TABLE 1-continued

| Amino Acid Sequence (SEQ ID NO:) | Position in HSP70 | Binding Prediction Score To A*24: 02 | To A*02: 01 | To A*02: 06 |
|---|---|---|---|---|
| FYPEEISSM (SEQ ID NO: 3) | 114 | 5.4008 | 4.1076 | 4.6748 |
| KLLQDFFNG (SEQ ID NO: 4) | 348 | 4.9877 | 4.8334 | 4.7267 |
| VLVGGSTRI (SEQ ID NO: 5) | 335 | 4.9353 | 4.6469 | 4.8296 |
| MVLTKMKEI (SEQ ID NO: 6) | 122 | 4.7341 | 4.1818 | 5.093 |
| YGAAVQAAI (SEQ ID NO: 7) | 371 | 4.6632 | 4.9012 | 4.2215 |
| LLLDVAPLS (SEQ ID NO: 8) | 392 | 4.4106 | 5.5399 | 5.3719 |
| AMTKDNNLL (SEQ ID NO: 9) | 448 | 5.6852 | 4.9114 | 3.9638 |
| ITRARFEEL (SEQ ID NO: 10) | 297 | 5.0063 | 3.8722 | 5.0269 |
| NLLGRFELS (SEQ ID NO: 11) | 454 | 4.3151 | 5.0725 | 5.4672 |
| AQIHDLVLV (SEQ ID NO: 12) | 329 | 4.1429 | 5.0029 | 5.5161 |
| YAFNMKSAV (SEQ ID NO: 13) | 545 | 3.1481 | 5.0986 | 5.022 |
| NQPGVLIQV (SEQ ID NO: 14) | 434 | 3.9589 | 5.2086 | 6.1881 |
| SVTNAVITV (SEQ ID NO: 15) | 138 | 3.4149 | 4.8686 | 6.0256 |

The peptide of the present invention has an HLA-binding capacity and has immunogenicity (hereinafter sometimes simply referred to as "HLA peptide" or "immunogenic peptide"). As used herein, "immunogenicity" means the ability to induce an immune response and, for example, means having a CTL-inducing activity and consequently having a cytotoxic activity against cancer cells.

In a preferred embodiment, the peptide of the present invention is a multi-HLA peptide capable of binding to a plurality of allelotypes of HLA-A gene A. For example, the peptide of SEQ ID NO: 7 strongly binds to a product of HLA-A*24:02 gene (an HLA-A*24:02 molecule), a product of HLA-A*02:01 gene (an HLA-A*02:01 molecule), and a product of HLA-A*02:06 gene (an HLA-A*02:06 molecule), and has high immunogenicity.

The HLA subtype to which the peptide of the present invention can bind is not limited to HLA-A*24:02, HLA-A*02:01, or HLA-A*02:06. However, these HLA subtypes cover the order of 85% of oriental people including the Japanese and on the order of 55% of western people; thus, it is considered that the multi-HLA peptide of the present invention achieves a broad patient coverage, for example, in immunotherapy.

The peptide of the present invention may be modified in the amino acid residues constituting the amino acid sequence of any of SEQ ID NOS: 1 to 15 or a part thereof as long as it retains immunogenicity. The amino acid sequence of each of SEQ ID NOS: 1 to 15 intends a state which is presented on an antigen-presenting cell; however, when the peptide of the present invention is directly administered into the body, the peptide sometimes experiences changes, such as the digestion of its terminal in digestive organs and the like, depending on the administration route. Thus, before incorporation into an antigen-presenting cell, the peptide of the present invention may be present in the form of a precursor which is formed by adding one or more amino acid residues or the like at the N-terminal and/or C-terminal so that amino acid sequence of any of SEQ ID NOS: 1 to 15 are retained upon binding to a predetermined HLA class I molecule on the antigen-presenting cell.

In addition, the peptide of the present invention may have 1 or several amino acid residues constituting the peptide of the present invention substituted, inserted, deleted, or added, and/or have modifications, such as sugar chain addition, side chain oxidation, and/or phosphorylation, as long as the peptide has desired immunogenicity. "Amino acid" herein is used in its most comprehensive sense and includes artificial amino acid variants and derivatives in addition to natural amino acids. Examples of the amino acid herein include natural protein L-amino acids; D-amino acids; chemically modified amino acids, such as amino acid variants and derivatives; natural non-protein amino acids, such as norleucine, β-alanine, and ornithine; and chemically synthesized compounds having properties known in the art, characteristic of amino acids. Examples of the non-natural amino acid include α-methyl amino acids (e.g., α-methylalanine), D-amino acids, histidine-like amino acids (e.g., β-hydroxyhistidine, homohistidine, α-fluoromethyl-histidine, and α-methyl-histidine), amino acids having extra methylene on the side chain ("homo" amino acids), and amino acids in each of which the carboxylic acid functional group on the side chain is substituted by a sulfonic acid group (e.g., cysteic acid).

For the substitution of an amino acid residue, and the like, in consideration of the regularity of a peptide sequence having a binding capacity to HLA (J. Immunol., 152: p 3913, 1994; Immunogenetics, 41: p 178, 1995; J. Immunol., 155: p 4307, 1994), those skilled in the art can properly substitute an amino acid residue as a constituent of the peptide of the present invention.

More specifically, in the case of a peptide binding to an HLA-A*24:02 molecule, the amino acid at position 2 of the peptide may be substituted by tyrosine, phenylalanine, methionine, or tryptophan, and/or the C-terminal amino acid may be substituted by phenylalanine, leucine, isoleucine, tryptophan, or methionine. In the case of a peptide binding to an HLA-A*02:01 molecule, the amino acid at position 2 may be substituted by leucine or methionine, and/or the C-terminal amino acid may be substituted by valine or leucine. In addition, in the case of a peptide binding to an HLA-A*02:06 molecule, the amino acid at position 2 may be substituted by valine or glutamine, and/or the C-terminal amino acid may be substituted by valine or leucine.

Each peptide of the present invention can be produced using a technique known to those skilled in the art. For example, it may be artificially synthesized by a solid-phase method, such as the Fmoc method or the tBoc method, or a liquid-phase method. A desired peptide may also be produced by expressing a polynucleotide encoding the peptide of the present invention or a recombinant vector containing the polynucleotide. The peptides thus obtained can each be identified using a technique known to those skilled in the art. For example, it can be identified using the Edman degradation method or a mass spectrometry method.

2. Pharmaceutical Composition

The pharmaceutical composition for treating or preventing cancer according to the present invention contains, as an active ingredient, for example, a peptide containing 8 or more consecutive amino acid residues in one or more amino acid sequences selected from the group consisting of SEQ ID NOS: 1 to 15 and consisting of 11 or less, preferably 10 or less, more preferably 9 or less amino acid residues in total. The peptide contained in the pharmaceutical composition may be a peptide consisting of an amino acid sequence of any of SEQ ID NOS: 1 to 15. The peptide is as defined hereinbefore.

The peptide of the present invention induces CTL by being presented on an antigen-presenting cell, and the induced CTL injures a cancer cell. Thus, the active ingredient of the pharmaceutical composition of the present invention is not limited to the peptide of the present invention, and may be a component capable of directly or indirectly inducing CTL, for example, a polynucleotide encoding the peptide or a vector containing the polynucleotide, or an antigen-presenting cell presenting a complex of the peptide and an HLA molecule on the surface or an exosome secreted from the antigen-presenting cell, or a combination thereof. Examples of the antigen-presenting cell used include a macrophage and a dendritic cell; however, it is preferable to use the dendritic cell, which has a high CTL-inducing capability. Any of other ingredients known to be used for cancer therapy, such as a chemokine, a cytokine, a tumor necrosis factor, and a chemotherapeutic agent, may be contained in the pharmaceutical composition of the present invention. The dose of the peptide may be, for example, about 1 to 10 mg per day when the patient is an adult. However, the dose varies depending on the age and body weight of the patient, the administration method, and the like, and thus is properly determined by those skilled in the art.

The pharmaceutical composition of the present invention is thought to be useful for the killing of cancer cells by, for example, but not intended to be limited to, the following action mechanism. The administration of the pharmaceutical composition of the present invention to a particular cancer patient results in that the peptide in the pharmaceutical composition is presented in a state in which it is bound to an HLA molecule on the antigen-presenting cell surface. On recognizing the peptide on such an antigen-presenting cell, CTL is activated, proliferated, and systemically circulated. When the peptide-specific CTL enters cancer tissue, it recognizes the same peptide derived from a specific cancer antigen, naturally binding to an HLA molecule present on the cancer cell surface to kill the cancer cell. Such an action contributes to the cancer treatment.

The pharmaceutical composition of the present invention can be used not only for treating cancer but also for preventing cancer. For example, the administration of the pharmaceutical composition of the present invention into a healthy human body induces CTL, and the induced cytotoxic T cell stay in the body and thus, when a particular cancer cell occurs, can injure the cancer cell. Similarly, the composition may be administered into a human body after treating cancer to prevent the recurrence of the cancer.

Any cancer expressing HSP70 is contemplated as a cancer to be treated or prevented. More specific examples of the cancer of interest include, but not intended to be limited to, pancreatic cancer, hepatocellular cancer, prostatic cancer, pulmonary cancer, mammary cancer, colonic cancer, hematological cancer, cerebral tumor, renal cancer, and cutaneous cancer. For example, since HSP70 from which the peptide of the present invention is derived is overexpressed in hepatocellular cancer, it is considered that the peptide of the present invention is effective particularly in treating or preventing the hepatocellular cancer. When a plurality of cancers to be treated or prevented are present, a plurality of active ingredients, including the immunogenic peptide, may be contained in the pharmaceutical composition of the present invention.

The pharmaceutical composition of the present invention can be dissolved in an aqueous solvent, formulated in the form of a pharmaceutically acceptable salt, and administered to patients. Examples of the form of such a pharmaceutically acceptable salt include a form buffered at physiological PH in the form of a physiologically acceptable water-soluble salt, for example, a salt of sodium, potassium, magnesium, or calcium. In addition to the water-soluble solvent, a non-water-soluble solvent may also be used; examples of such a non-water-soluble solvent include alcohols, such as ethanol and propylene glycol.

The formulation containing the pharmaceutical composition of the present embodiment may contain agents for various purposes; examples of such agents include a preservative and a buffer agent. Examples of the preservative include sodium bisulfite, sodium bisulfate, sodium thiosulfate, benzalkonium chloride, chlorobutanol, thimerosal, phenylmercuric acetate, phenylmercuric nitrate, methylparaben, polyvinyl alcohol, phenylethyl alcohol, ammonia, dithiothreitol, and beta-mercaptoethanol. Examples of the buffer agent include sodium carbonate, sodium borate, sodium phosphate, sodium acetate, and sodium bicarbonate. These agents can be present in an amount capable of maintaining the pH of a system at 2 to 9, preferably 4 to 8.

The dosage form of the pharmaceutical composition of the present invention is not particularly limited; however, when it is used in the form of a vaccine, examples of its dosage form include injections (intramuscular, subcutaneous, and intracutaneous), oral formulations, and nasal drop formulations. When the pharmaceutical composition of the present invention is in the form of a vaccine, it may be a mixed cocktail vaccine containing a plurality of active ingredients. For example, such a vaccine can contain any two or more of the peptides of SEQ ID NOS: 1 to 15, or contain a plurality of active ingredients by combination with other active ingredients.

The vaccine of the present invention may be an inert ingredient-containing vaccine containing an ingredient which is an ingredient other than the pharmaceutical composition, has no activity per se, and has the effect of further enhancing the effect of the pharmaceutical composition as a vaccine. Examples of the inert ingredient include an adjuvant and a toxoid. Examples of the adjuvant include, but not intended to be limited to, precipitation type ones, such as aluminium hydroxide, aluminium phosphate, and calcium phosphate, and oily type ones, such as Freund's complete adjuvant and Freund's incomplete adjuvant.

When present in the form of a vaccine, the pharmaceutical composition of the present invention is preferably administered into the body by injection or infusion, such as intracutaneous, subcutaneous, or intramuscular administration, or by dermal administration or inhalation through the mucosa of the nose, pharynx, or the like. Its single dose can be set to between a dose capable of significantly inducing cytotoxic T cells and a dose at which a significant number of non-cancer cells experience injury.

The pharmaceutical composition of the present invention is contemplated for not only administration to a human body but also extracorporeal use. More specifically, the pharmaceutical composition of the present invention may be used for the purpose of stimulating an antigen-presenting cell in vitro or ex vivo to increase its CTL-inducing activity. For example, in a case where the pharmaceutical composition of the present invention is used for dendritic cell therapy for cancer, the composition can be contacted with antigen-presenting cells, such as dendritic cells, derived from a patient in need of cancer treatment or prevention in advance, followed by administering the antigen-presenting cells to the patient by returning them into the patient's body. The peptide contained in the pharmaceutical composition can be introduced into an antigen-presenting cell, for example, by a lipofection method or an injection method. When a polynucleotide encoding the peptide of the present invention is used in such an application, the polynucleotide can be introduced into an antigen-presenting cell by a technique known in the art. For example, an antigen-presenting cell derived from a patient may be transformed in vitro using a polynucleotide of interest or a vector encoding the polynucleotide by a lipofection method, an electroporation method, a microinjection method, a cell fusion method, a DEAE dextran method, a calcium phosphate method, or the like.

3. Immunity Inducer

The immunity inducer according to the present invention contains, as an active ingredient, for example, a peptide containing 8 or more consecutive amino acid residues in one or more amino acid sequences selected from the group consisting of SEQ ID NOS: 1 to 15, and consisting of 11 or less, preferably 10 or less, more preferably 9 or less amino acid residues in total. The peptide contained in the immunity inducer may be a peptide consisting of an amino acid sequence of any of SEQ ID NOS: 1 to 15. The peptide is as defined hereinbefore.

It is considered that the peptide of the present invention induces immunity by being presented on an antigen-presenting cell. Thus, the active ingredient of the immunity inducer of the present invention is not limited to the peptide of the present invention, and may be a component capable of directly or indirectly inducing immunity, for example, a polynucleotide encoding the peptide of the present invention or an expression vector containing the peptide, or an antigen-presenting cell presenting a complex of the peptide and an HLA molecule on the surface or an exosome secreted from the antigen-presenting cell, or a combination thereof. Examples of the antigen-presenting cell used include a macrophage and a dendritic cell; however, it is preferable to use the dendritic cell, which has a high CTL-inducing capability.

The immunity inducer of the present invention is contemplated for not only administration to a human body but also extracorporeal use. More specifically, the immunity inducer of the present invention may be used for the purpose of stimulating an antigen-presenting cell in vitro or ex vivo to increase its CTL-inducing activity. For example, in a case where the immunity inducer of the present invention is used for dendritic cell therapy, the inducer can be contacted with antigen-presenting cells, such as dendritic cells, derived from a patient in need of immunity induction in advance, followed by administering the antigen-presenting cells to the patient by returning them into the patient's body. The peptide contained in the immunity inducer can be introduced into an antigen-presenting cell, for example, by transfection via a liposome (a lipofection method) or an injection method. When a polynucleotide encoding the peptide of the present invention is used in such an application, the polynucleotide can be introduced into an antigen-presenting cell by a technique known in the art. For example, an antigen-presenting cell derived from a patient may be transformed in vitro using a polynucleotide of interest or a vector expressing the polynucleotide by a lipofection method, an electroporation method, a microinjection method, a cell fusion method, a DEAE dextran method, a calcium phosphate method, or the like.

As used herein, "immunity induction" means inducing an immune response, for example, increasing the CTL-inducing activity of an antigen-presenting cell, and further increasing the cytotoxic activity of CTL against a cancer cell. As used herein, "CTL induction" means inducing or proliferating CTL specifically recognizing a certain antigen, or differentiating a naive T cell into an effector cell having the ability to kill a target cell (cytotoxic activity), such as a cancer cell, and/or increasing the cytotoxic activity of CTL by the presentation of the peptide of the present invention on the antigen-presenting cell surface in vitro or in vivo. The CTL-inducing activity can be measured by evaluating the production of cytokines (for example, interferon (IFN)-$\gamma$) by CTL. For example, the CTL-inducing activity may be measured by evaluating an increase in cytokine-producing cells induced from precursor cells by antigen-presenting cells, such as peripheral-blood monocytes, stimulated with the peptide of the present invention, using a known high-sensitive immunoassay, such as ELISPOT (Enzyme-Linked ImmunoSpot). The cytotoxic activity can also be measured by a known method, such as a $^{51}$Cr release method. When the activity is significantly increased, for example, by 5% or more, 10% or more, 20% or more, preferably 50% or more, compared to control, immunity or CTL can be evaluated to have been induced.

4. Method for Producing Antigen-Presenting Cell

The method for producing an antigen-presenting cell according to the present invention includes a step of contacting, for example, a peptide containing 8 or more consecutive amino acid residues in one or more amino acid sequences selected from the group consisting of SEQ ID NOS: 1 to 15, and consisting of 11 or less, preferably 10 or less, more preferably 9 or less amino acid residues in total, with an antigen-presenting cell in vitro. The peptide used in the production method of the present invention may be a peptide consisting of an amino acid sequence of any of SEQ ID NOS: 1 to 15. The peptide is as defined hereinbefore.

It is considered that the peptide used in the production method of the present invention binds to an HLA class I molecule on the antigen-presenting cell surface, is presented to CTL as an antigen peptide, and thereby induces the CTL activity of the antigen-presenting cell. Thus, the component to be contacted with an antigen-presenting cell is not limited to the peptide of the present invention, and may be a component capable of directly or indirectly inducing CTL, for example, a polynucleotide encoding the peptide or a vector containing the polynucleotide, or an antigen-presenting cell presenting a complex of the peptide and an HLA molecule on the surface or an exosome secreted from the antigen-presenting cell, or a combination thereof. Examples of the antigen-presenting cell used include a macrophage and a dendritic cell; however, it is preferable to use the dendritic cell, which has a high CTL-inducing capability.

The antigen-presenting cell produced by the production method of the present invention is contemplated to be not only used as an active ingredient of the pharmaceutical composition or the immunity inducer but also used for immunotherapy and the like. For example, in a case where the antigen-presenting cells produced are used for dendritic cell therapy for cancer, the cells can be contacted with antigen-presenting cells, such as dendritic cells, having a low CTL-inducing capability, derived from a patient in need of immunity induction in advance, followed by administering the antigen-presenting cells to the patient by returning them into the patient's body. The peptide of the present invention can be introduced into an antigen-presenting cell, for example, by transfection via a liposome (a lipofection method) or an injection method. When a polynucleotide encoding the peptide of the present invention is used in such an application, the polynucleotide can be introduced into an antigen-presenting cell by a technique known in the art. For example, an antigen-presenting cell derived from a patient may be transformed in vitro using a polynucleotide of interest or a vector encoding the polynucleotide by a lipofection method, an electroporation method, a microinjection method, a cell fusion method, a DEAE dextran method, a calcium phosphate method, or the like.

EXAMPLE 1

The present invention will be more specifically described below with reference to Examples. However, the present invention is not intended to be limited thereto.

Specifically, the procedures of prediction, experiment, and evaluation in this Example were carried out based on the active learning experiment design described in International Publication No. WO 2006/004182. A rule was constructed by repeating the following steps as a whole.

(1) A low rank learning algorithm to be described hereinafter is once tried. That is, a plurality of hypotheses are generated based on random resampling from accumulated data, and the point is chosen at which the variance of predicted values of randomly generated candidate query points (peptides) is largest as the query point to be experimented.

(2) The peptide at the chosen query point is produced by synthesis and purification methods to be described hereinafter. The actual binding capacity is measured by an experiment to be described hereinafter, and added to the accumulated data.

Performing such an active learning method could reduce the number of binding experiments which are otherwise necessary to carry out for all of 5 hundred billion ($=20^9$) or more candidate substances of HLA-binding peptides consisting of 9 amino acid residues.

Using the rule as described above, the amino acid sequences of SEQ ID NOS: 1 to 15 were extracted.

Synthesis and Purification of Peptide

The peptides having the amino acid sequences of SEQ ID NOS: 1 to 15 were manually synthesized by the Merrifield solid-phase method using Fmoc amino acids. The resultant were deprotected and then subjected to reverse-phase HPLC purification using a C18 column to a purity of 95% or more. The identification of the peptides and confirmation of the purity thereof were performed by MALDI-TOF mass spectrometry (AB SCIEX MALDI-TOF/TOF5800). Peptide quantification was carried out by Micro BCA assay (Thermo Scienftific Co., Ltd.) using BSA as a standard protein.

Binding Experiment of Peptide to HLA-A*24:02 Molecule

The binding capacity of each peptide to the HLA-A*24:02 molecule as the product of HLA-A*24:02 gene was measured using C1R-A24 cells expressing the HLA-A*24:02 molecule (the cells prepared by Prof. Masafumi Takeguchi, Kumamoto University were gifted by Assoc. Prof. Masaki Yasukawa, Ehime University with permission).

First, C1R-A24 cells were exposed to acidic conditions of pH 3.3 for 30 seconds to dissociate and remove endogenous peptides which were originally bound to the HLA-A*24:02 molecule and a light chain, β2m, which was commonly associated with HLA class I molecules. After neutralization, purified β2m was added to the C1R-A24 cells, which was then added to peptide dilution series. The mixtures were each then incubated on ice for 4 hours. The 3-molecule assembly (MHC-pep) consisting of the HLA-A*24:02 molecule, the peptide, and β2 m which had been reasociated during the incubation was stained with a fluorescent labeled monoclonal antibody, 17A12, recognizing the assembly.

Subsequently, the number of MHC-pep's per C1R-A24 cell (which is proportional to the fluorescent intensity of the above fluorescent antibody) was quantitatively measured using a fluorescent cell analyzer, FACScan (Becton, Dickinson and Company). The binding dissociation constant, Kd value, between the HLA-A*24:02 molecule and the peptide was calculated from the average fluorescent intensity per cell using a method as published in a paper (Udaka et al., Immunogenetics, 51, 816-828, 2000) by the present inventor.

Binding Experiment of Peptide to HLA-A*02:01 Molecule

The binding capacity of each peptide to the HLA-A*02:01 molecule as the product of HLA-A*02:01 gene was measured using a cell line, T2, (purchased from ATCC) expressing the HLA-A*02:01 molecule.

T2 cells and purified β2m were added to stepwise dilution series of a peptide whose binding capacity was to be measured, which was then incubated at 37° C. for 4 hours. The HLA-A*02:01 molecule whose expression level was concentration-dependently increased by this time point was stained with an assembly-specific fluorescent labeled monoclonal antibody, BB7.2.

Thereafter, the amount of fluorescence per cell was measured using a flow cytometer, and the dissociation constant, Kd value, was calculated using a method as published in a paper by the present inventor (Udaka et al., Immunogenetics, 51, 816-828, 2000).

Binding Experiment of Peptide to HLA-A*02:06 Molecule

The binding capacity of each peptide to the HLA-A*02:06 molecule as the product of HLA-A*02:06 gene was measured using RA2.6 cells (a cell line newly prepared at Kochi University) in which cDNA of the HLA-A*02:06 gene was introduced into RMAS as a mouse TAP (transporter associated with antigen processing)-deficient cell line.

First, the RA2.6 cells were cultured overnight at 26° C. to accumulate the HLA-A*02:06 molecules unbound to the peptide on the cell surface. Any of peptide dilution series was added thereto for binding at 26° C. for 60 minutes.

Subsequently, the mixture was cultured at 35° C. for 4 hours, resulting in the denaturation of the empty HLA-A*02:06 molecule unbound to the peptide and the loss of its steric structure. A fluorescent labeled monoclonal antibody, BB7.2, specifically recognizing a peptide-bound HLA-A*02:06 molecule, was added thereto, which was then incubated on ice for 20 minutes to stain the cells.

Thereafter, the amount of fluorescence per cell was measured using a flow cytometer, and the dissociation constant, Kd value, was calculated using a method as published in a paper by the present inventor (Udaka et al., Immunogenetics, 51, 816-828, 2000).

Evaluation Result of Binding Experiment

As a result, the binding experiment data of the peptides of the present invention to each HLA molecule as shown in the following table were obtained.

TABLE 2

| Amino Acid Sequence (SEQ ID NO:) | Position in HSP70 | Binding Experiment Data | | |
|---|---|---|---|---|
| | | To A*24: 02 | To A*02: 01 | To A*02: 06 |
| GVPQIEVTF (SEQ ID NO: 1) | 470 | -6.451225173 | >-3 | -5.130417023 |
| TFDVSILTI (SEQ ID NO: 2) | 204 | -6.238032253 | >-3 | >-3 |
| FYPEEISSM (SEQ ID NO: 3) | 114 | -7.66350091 | >-3 | >-3 |
| KLLQDFFNG (SEQ ID NO: 4) | 348 | >-3 | -4.958921074 | -5.268061867 |
| VLVGGSTRI (SEQ ID NO: 5) | 335 | -6.172930121 | -4.860260368 | -5.069659334 |
| MVLTKMKEI (SEQ ID NO: 6) | 122 | -5.818975521 | -4.58642391 | -5.532894759 |
| YGAAVQAAI (SEQ ID NO: 7) | 371 | -5.502072835 | -4.904317969 | -5.37221634 |
| LLLDVAPLS (SEQ ID NO: 8) | 392 | >-3 | -6.059683064 | -6.171355699 |
| AMTKDNNLL (SEQ ID NO: 9) | 448 | -5.492398754 | -5.559823762 | -4.275867751 |
| ITRARFEEL (SEQ ID NO: 10) | 297 | -5.206187958 | -4.325522946 | -5.579932749 |
| NLLGRFELS (SEQ ID NO: 11) | 454 | >-3 | -4.559640805 | -5.175394643 |
| AQIHDLVLV (SEQ ID NO: 12) | 329 | >-3 | -6.147821579 | -6.44597639 |
| YAFNMKSAV (SEQ ID NO: 13) | 545 | >-3 | -5.09069 | -5.020701151 |
| NQPGVLIQV (SEQ ID NO: 14) | 434 | >-3 | -5.909585202 | -6.417158659 |

TABLE 2-continued

| Amino Acid Sequence (SEQ ID NO:) | Position in HSP70 | Binding Experiment Data | | |
|---|---|---|---|---|
| | | To A*24: 02 | To A*02: 01 | To A*02: 06 |
| SVTNAVITV (SEQ ID NO: 15) | 138 | -4.370281453 | -4.76157 | -5.594226356 |

The amino acid sequences of SEQ ID NOS: 1 to 15 are derived from the full-length sequence of the predetermined genomic protein of HSP70 shown in SEQ ID NO: 16.

Immunity Induction Test of Peptide (1) Preparation of Peptide-Stimulated Dendritic Cell
Day 0 to 9 (Induction of Dendritic Cell)
Monocytes were separated from the peripheral blood collected from a hepatocellular cancer patient according to a leukapheresis method. The separated monocytes were cultured for 6 days under addition of 800 U/ml GM-CSF and 500 U/ml IL-4. In addition, 300 U/ml TNF-α was added to the culture solution, which was then cultured for 4 days to induce mature dendritic cells. Subsequently, HSP70 mRNA was introduced thereinto by an electroporation method and thereby dendritic cells having presented an HSP70-derived antigen peptide were prepared.

Dendritic cells into which $1\times10^7$, $2\times10^7$, or $3\times10^7$ HSP70 mRNAs were introduced (HSP70-dendritic cells) were administered into the thigh of the hepatocellular cancer patient by subcutaneous injection (HSP70 dendritic cell therapy). The subcutaneous administration of the HSP70-dendritic cells prepared by the same method was repeated every 3 weeks. Of peripheral blood monocytes obtained by pheresis from the liver cancer patient treated 2 times or more with HSP70 dendritic cell therapy, a cell fraction adhering to the culture flask was cultured in AIM-CM medium (trade name "Gibco" from Thermo Fisher Scientific Co., Ltd.) at 37° C. for 10 days. During culture, 15 µl of IL-4 and 30 µl of granulocyte-monocyte colony-stimulating factor (GM-CSF) were added to the medium at day 0 and day 3, and 15 µl of IL-4, 30 µl of GM-CSF, and 75 µl of tumor necrosis factor (TNF)-α were added at day 5.

Day 10 (Stimulation with Peptide and Recovery of Dendritic Cell)
The dendritic cells induced from monocytes were newly recovered into AIM-CM medium, and the peptides of the present invention (SEQ ID NOS: 5, 6, 7, 9, 10, and 15) were each added to 20 µg/ml. Then, the medium containing the dendritic cells was cultured at 37° C. for 2 hours. The following peptides were used as positive and negative controls.

Positive control for HLA-A24:02 (EBV LMP2, 419-427: TYGPVFMCL (SEQ ID NO: 17))
Negative control for HLA-A24:02 (HIV env gp160, 584-592: RYLRDQQLL (SEQ ID NO: 18))
Positive control for HLA-A02:01 (Flu A MP, 58-66: GILGFVFTL (SEQ ID NO: 19))
Negative control for HLA-A02:01 (HIV gap p17, 77-85: SLYNTVATL (SEQ ID NO: 20))
Positive control for HLA-A02:06 (EBV LMP2 453-461: LTAGFLIFL (SEQ ID NO: 21))
Negative control for HLA-A02:06 (HIV gap p 24 341-349: ATLEEMMTA (SEQ ID NO: 22))

The dendritic cells were recovered, washed 3 times or more with a sufficient amount of AIM-CM medium, and counted.

(2) Preparation of CD8T Cell
Day 0 to 9
Of peripheral blood monocytes obtained by pheresis from the liver cancer patient treated 2 times or more with HSP70 dendritic cell therapy, a floating cell fraction (including lymphocytes) not adhering to the culture flask was cultured in AIM-CM medium (from GIBCO Co., Ltd.) at 37° C. for 10 days. During culture, 40 µl of IL-2 was added to the medium at day 4 and day 6.

Day 10
Using CD8 Negative Selection Kit (from Miltenyi Biotec), CD8T cells were separated from the medium and counted.

(3) Coculture
The dendritic cells and the CD8T cells obtained in (1) and (2) above were cocultured in AIM medium at 37° C. under the following conditions.
CD8T cells: $5\times10^5$ cells/well
Dendritic cells: $2\times10^5$ cells/well Day 12 or 13
To the above medium was added 0.4 ml/well of AIM-CM medium containing IL-2 in an amount of 20 U/ml.

(4) ELISPOT Assay
Day 17
The CD8T cells were added to a 96-well plate for ELISPOT (from Millipore), coated with an anti-IFN-γ monoclonal antibody (from Mabtech AB) to $2\times10^4$ cells/well. For each sample, 3 or more wells were used. To each well was added 100 µl of AIM-V (from trade name "Gibco" from Thermo Fisher Scientific Co., Ltd.). The 96-well plate for ELISPOT was cultured at 37° C.

Figure 2:
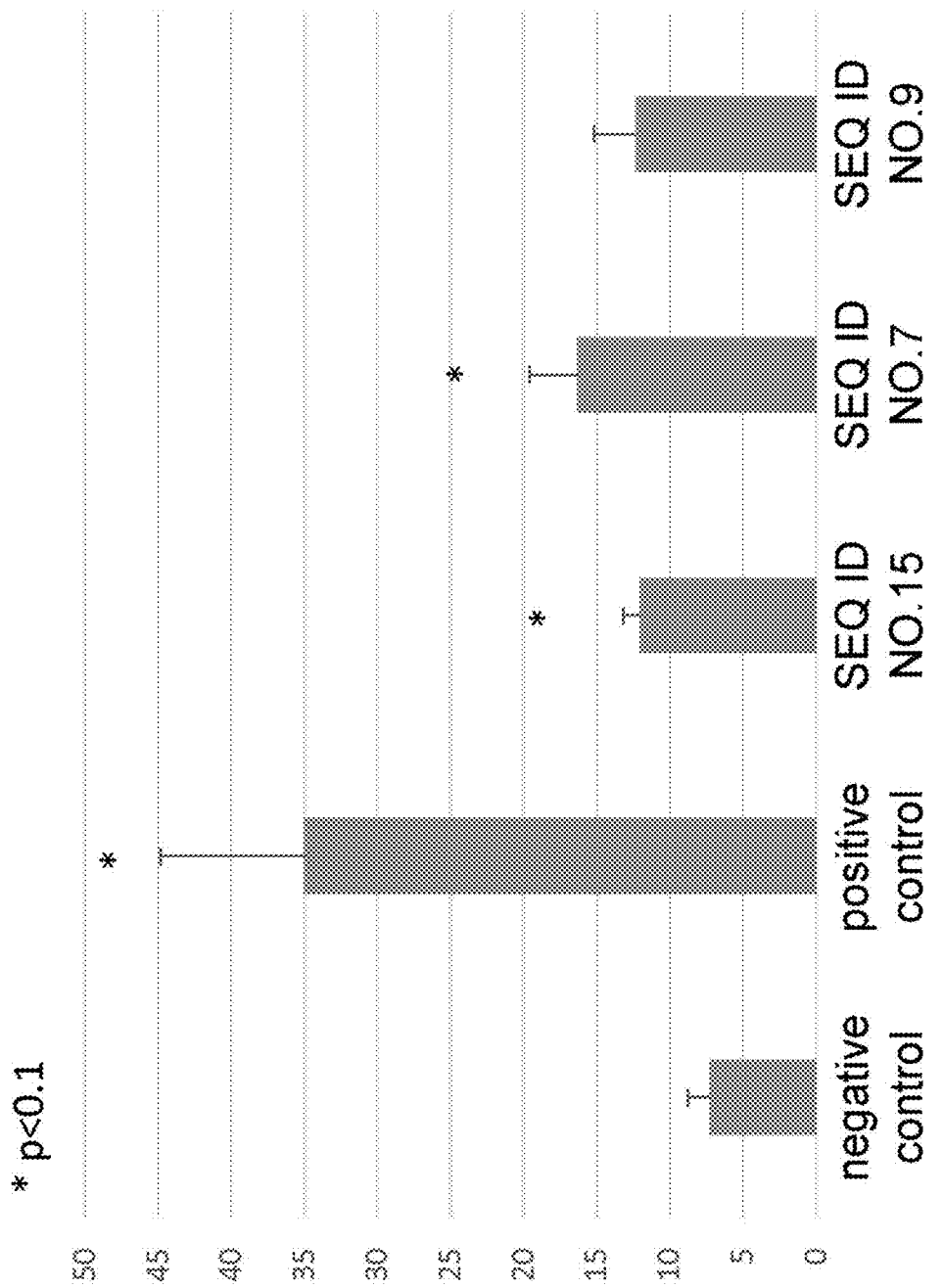
FIG. 2 is a graph showing the results of ELISPOT assay (the number of IFN-γ-producing cells) when samples derived from liver cancer patients (HLA type: 02:01/33:03) having received HSP70 dendritic cell therapy were stimulated with the peptide of SEQ ID NO: 7, 9, or 15.
Figure 3:
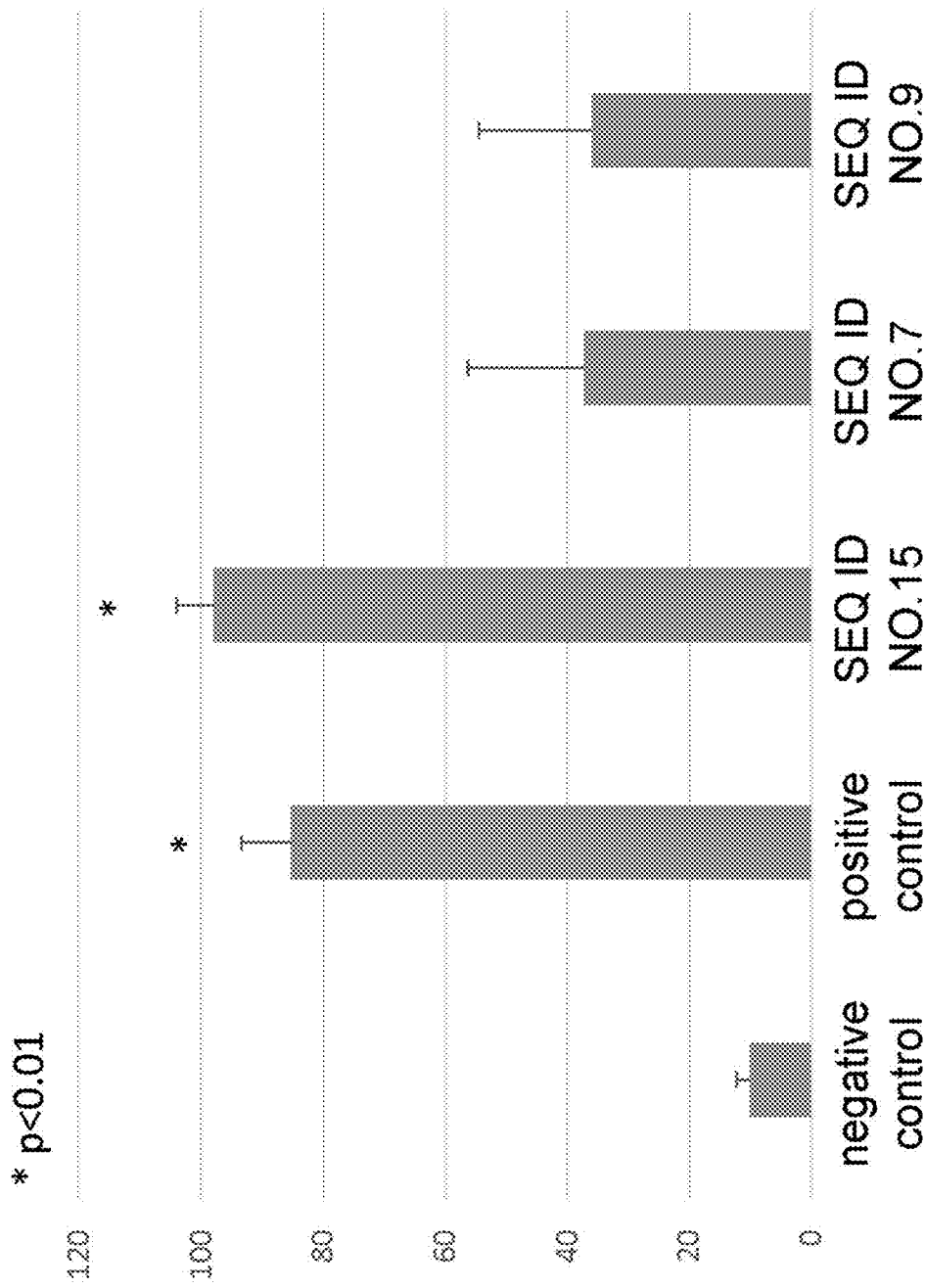
FIG. 3 is a graph showing the results of ELISPOT assay (the number of IFN-γ-producing cells) when samples derived from liver cancer patients (HLA type: 02:06/24:02) having received HSP70 dendritic cell therapy were stimulated with the peptide of SEQ ID NO: 7, 9, or 15.

Day 18
The anti-IFN-γ antibody was added to each well and further reacted with an HRP enzyme-labeled secondary antibody to measure the number of IFN-γ-producing cells by color reaction. As typical results of the ELISPOT assay, those for patients whose HLA type was 02:01/24:02 are shown in FIG. 1; those for patients, 02:01/33:03, in FIG. 2; and those for patients, 02:06/24:02, in FIG. 3. In each figure, the average of 5 assay results are indicated.

Figure 4:
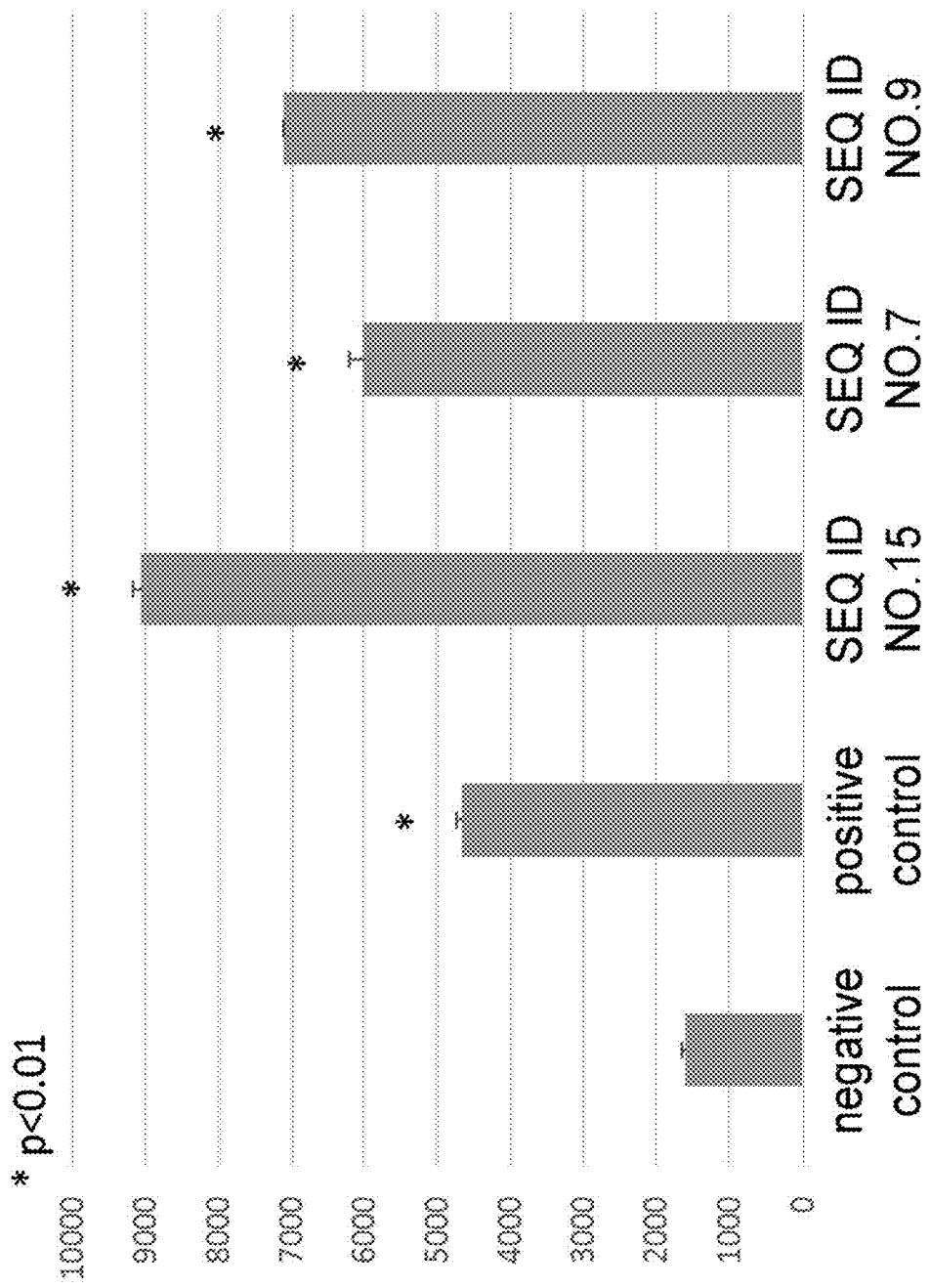
FIG. 4 is a graph showing the results of ELISA assay (the number of IFN-γ-producing cells) when samples derived from liver cancer patients (HLA type: 24:02/26:01) having received HSP70 dendritic cell therapy were stimulated with the peptide of SEQ ID NO: 7, 9, or 15.
Figure 5:
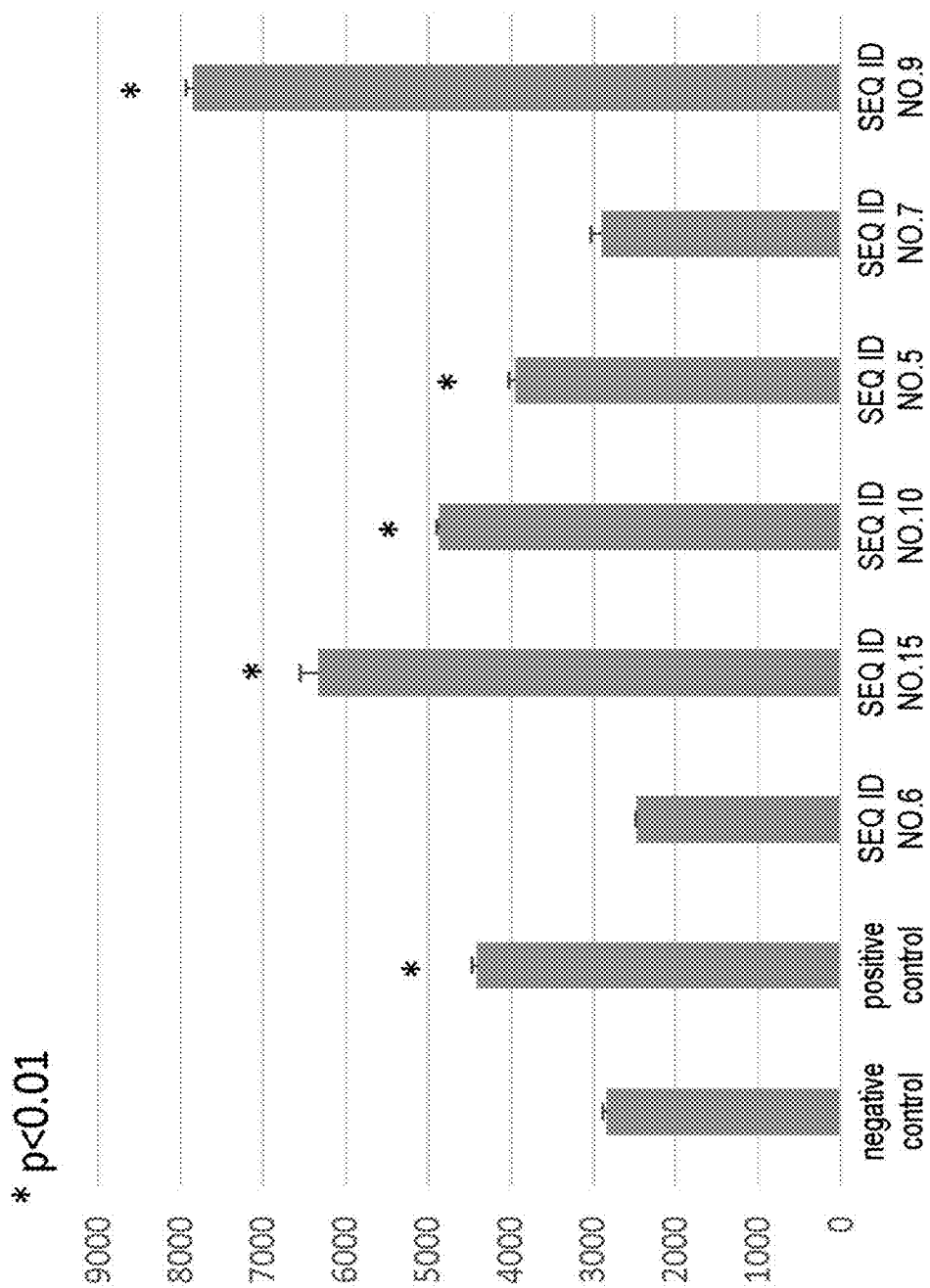
FIG. 5 is a graph showing the results of ELISA assay (the number of IFN-γ-producing cells) when samples derived from liver cancer patients (HLA type: 24:02/26:01) having received HSP70 dendritic cell therapy were stimulated with the peptide of SEQ ID NO: 5, 6, 7, 9, 10, or 15.
Figure 6:
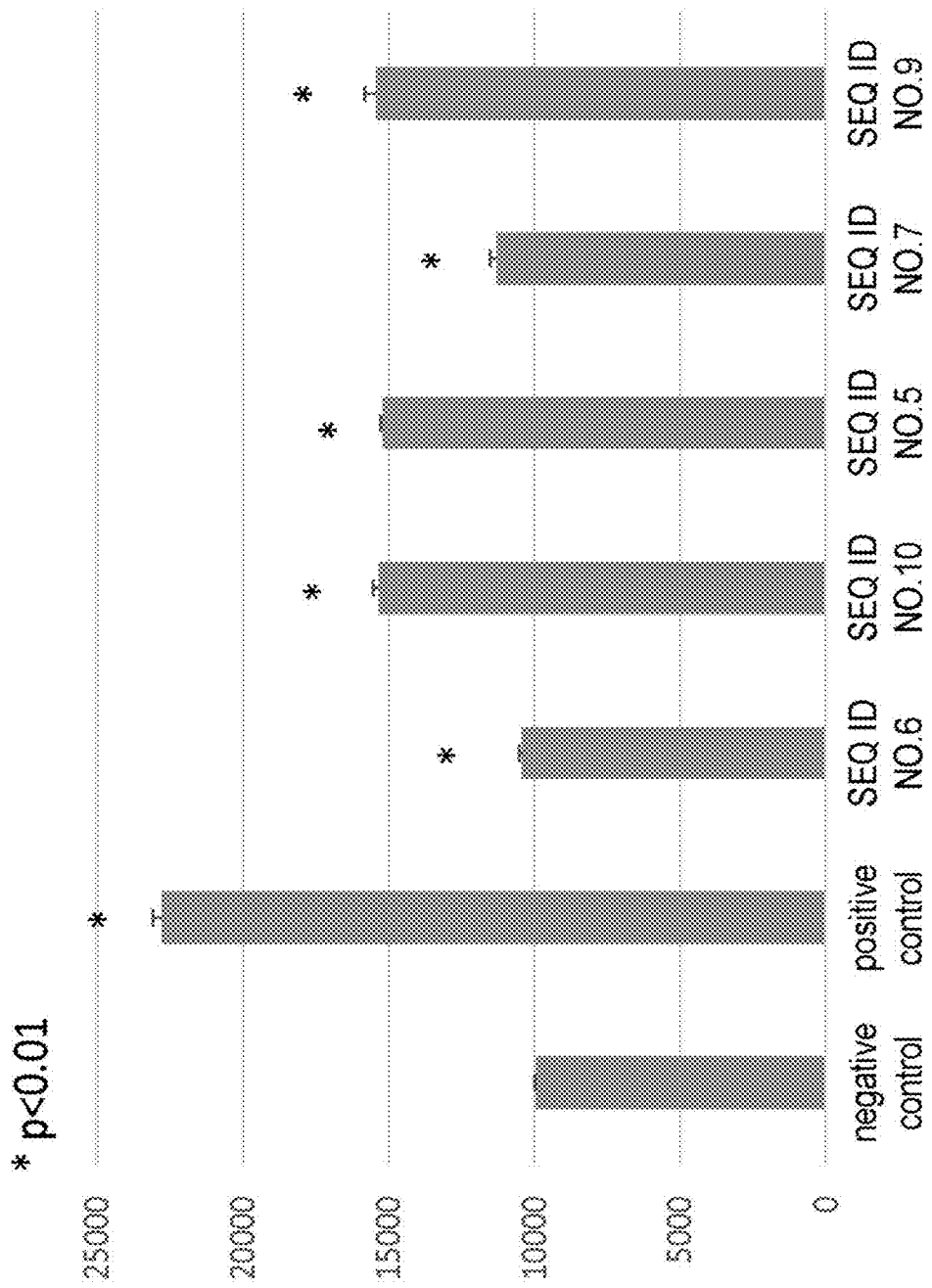
FIG. 6 is a graph showing the results of ELISA assay (the number of IFN-γ-producing cells) when samples derived from liver cancer patients (HLA type: 24:02/24:02) having received HSP70 dendritic cell therapy were stimulated with the peptide of SEQ ID NO: 5, 6, 7, 9, or 10.

(5) ELISA Assay
Day 17
A culture supernatant at day 7 after coculture of T cells with dendritic cells pulsed with each of the above peptides was diluted to the 4 levels of ×1, ×5, ×25, and ×125 to identify the dilution level falling within the limit of measurement using Human IFN-γ ELISA MAX Deluxe Set (from BioLegend Inc.). Thereafter, each sample was measured 3 times at the identified dilution level. As typical results of the ELISA assay, those for patients whose HLA type was 24:02/26:01 are shown in FIGS. 4 and 5 and those for patients, 24:02/24:02 in FIG. 6.

The present invention has been described above based on Example. This Example is merely illustrative, and it should be understood by those skilled in the art that various modifications may be made and that the modifications are also within the scope of the present invention.

The invention claimed is:

1. A method for inducing an immune response in a subject suffering from cancer, comprising a step of administrating to the subject a peptide consisting of the amino acid sequence of SEQ ID NO: 7.

2. The method according to claim 1, wherein the peptide can bind to one or more types of HLA molecules.

3. A method for inducing an immune response in a subject suffering from cancer, comprising a step of administrating to the subject a pharmaceutical composition comprising a peptide consisting of the amino acid sequence of SEQ ID NO: 7 and a pharmaceutically acceptable formulation component.

4. The method according to claim 3, wherein the pharmaceutical composition is in the form of a vaccine.

5. The method according to claim 4, wherein the peptide can bind to one or more types of HLA molecules.

* * * * *

SEQUENCE LISTING

<160> NUMBER OF SEQ ID NOS: 22

<210> SEQ ID NO 1
<211> LENGTH: 9
<212> TYPE: PRT
<213> ORGANISM: Homo sapiens

<400> SEQUENCE: 1

Gly Val Pro Gln Ile Glu Val Thr Phe
1               5

<210> SEQ ID NO 2
<211> LENGTH: 9
<212> TYPE: PRT
<213> ORGANISM: Homo sapiens

<400> SEQUENCE: 2

Thr Phe Asp Val Ser Ile Leu Thr Ile
1               5

<210> SEQ ID NO 3
<211> LENGTH: 9
<212> TYPE: PRT
<213> ORGANISM: Homo sapiens

<400> SEQUENCE: 3

Phe Tyr Pro Glu Glu Ile Ser Ser Met
1               5

<210> SEQ ID NO 4
<211> LENGTH: 9
<212> TYPE: PRT
<213> ORGANISM: Homo sapiens

<400> SEQUENCE: 4

Lys Leu Leu Gln Asp Phe Phe Asn Gly
1               5

<210> SEQ ID NO 5
<211> LENGTH: 9
<212> TYPE: PRT
<213> ORGANISM: Homo sapiens

<400> SEQUENCE: 5

Val Leu Val Gly Gly Ser Thr Arg Ile
1               5

<210> SEQ ID NO 6
<211> LENGTH: 9
<212> TYPE: PRT
<213> ORGANISM: Homo sapiens

<400> SEQUENCE: 6

Met Val Leu Thr Lys Met Lys Glu Ile
1               5

<210> SEQ ID NO 7
<211> LENGTH: 9
<212> TYPE: PRT
<213> ORGANISM: Homo sapiens

```
<400> SEQUENCE: 7

Tyr Gly Ala Ala Val Gln Ala Ala Ile
1               5

<210> SEQ ID NO 8
<211> LENGTH: 9
<212> TYPE: PRT
<213> ORGANISM: Homo sapiens

<400> SEQUENCE: 8

Leu Leu Leu Asp Val Ala Pro Leu Ser
1               5

<210> SEQ ID NO 9
<211> LENGTH: 9
<212> TYPE: PRT
<213> ORGANISM: Homo sapiens

<400> SEQUENCE: 9

Ala Met Thr Lys Asp Asn Asn Leu Leu
1               5

<210> SEQ ID NO 10
<211> LENGTH: 9
<212> TYPE: PRT
<213> ORGANISM: Homo sapiens

<400> SEQUENCE: 10

Ile Thr Arg Ala Arg Phe Glu Glu Leu
1               5

<210> SEQ ID NO 11
<211> LENGTH: 9
<212> TYPE: PRT
<213> ORGANISM: Homo sapiens

<400> SEQUENCE: 11

Asn Leu Leu Gly Arg Phe Glu Leu Ser
1               5

<210> SEQ ID NO 12
<211> LENGTH: 9
<212> TYPE: PRT
<213> ORGANISM: Homo sapiens

<400> SEQUENCE: 12

Ala Gln Ile His Asp Leu Val Leu Val
1               5

<210> SEQ ID NO 13
<211> LENGTH: 9
<212> TYPE: PRT
<213> ORGANISM: Homo sapiens

<400> SEQUENCE: 13

Tyr Ala Phe Asn Met Lys Ser Ala Val
1               5

<210> SEQ ID NO 14
<211> LENGTH: 9
<212> TYPE: PRT
<213> ORGANISM: Homo sapiens

<400> SEQUENCE: 14
```

```
Asn Gln Pro Gly Val Leu Ile Gln Val
1               5
```

<210> SEQ ID NO 15
<211> LENGTH: 9
<212> TYPE: PRT
<213> ORGANISM: Homo sapiens

<400> SEQUENCE: 15

```
Ser Val Thr Asn Ala Val Ile Thr Val
1               5
```

<210> SEQ ID NO 16
<211> LENGTH: 641
<212> TYPE: PRT
<213> ORGANISM: Homo sapiens

<400> SEQUENCE: 16

```
Met Ala Lys Ala Ala Val Gly Ile Asp Leu Gly Thr Thr Tyr Ser
1               5                   10                  15

Cys Val Gly Val Phe Gln His Gly Lys Val Glu Ile Ile Ala Asn Asp
                20                  25                  30

Gln Gly Asn Arg Thr Thr Pro Ser Tyr Val Ala Phe Thr Asp Thr Glu
        35                  40                  45

Arg Leu Ile Gly Asp Ala Ala Lys Asn Gln Val Ala Leu Asn Pro Gln
50                  55                  60

Asn Thr Val Phe Asp Ala Lys Arg Leu Ile Gly Arg Lys Phe Gly Asp
65                  70                  75                  80

Pro Val Val Gln Ser Asp Met Lys His Trp Pro Phe Gln Val Ile Asn
                85                  90                  95

Asp Gly Asp Lys Pro Lys Val Gln Val Ser Tyr Lys Gly Glu Thr Lys
            100                 105                 110

Ala Phe Tyr Pro Glu Glu Ile Ser Ser Met Val Leu Thr Lys Met Lys
        115                 120                 125

Glu Ile Ala Glu Ala Tyr Leu Gly Tyr Ser Val Thr Asn Ala Val Ile
    130                 135                 140

Thr Val Pro Ala Tyr Phe Asn Asp Ser Gln Arg Gln Ala Thr Lys Asp
145                 150                 155                 160

Ala Gly Val Ile Ala Gly Leu Asn Val Leu Arg Ile Ile Asn Glu Pro
                165                 170                 175

Thr Ala Ala Ala Ile Ala Tyr Gly Leu Asp Arg Thr Gly Lys Gly Glu
            180                 185                 190

Arg Asn Val Leu Ile Phe Asp Leu Gly Gly Gly Thr Phe Asp Val Ser
        195                 200                 205

Ile Leu Thr Ile Asp Asp Gly Ile Phe Glu Val Lys Ala Thr Ala Gly
    210                 215                 220

Asp Thr His Leu Gly Gly Glu Asp Phe Asp Asn Arg Leu Val Asn His
225                 230                 235                 240

Phe Val Glu Glu Phe Lys Arg Lys His Lys Lys Asp Ile Ser Gln Asn
                245                 250                 255

Lys Arg Ala Val Arg Arg Leu Arg Thr Ala Cys Glu Arg Ala Lys Arg
            260                 265                 270

Thr Leu Ser Ser Ser Thr Gln Ala Ser Leu Glu Ile Asp Ser Leu Phe
        275                 280                 285

Glu Gly Ile Asp Phe Tyr Thr Ser Ile Thr Arg Ala Arg Phe Glu Glu
    290                 295                 300
```

```
Leu Cys Ser Asp Leu Phe Arg Ser Thr Leu Glu Pro Val Glu Lys Ala
305                 310                 315                 320

Leu Arg Asp Ala Lys Leu Asp Lys Ala Gln Ile His Asp Leu Val Leu
            325                 330                 335

Val Gly Gly Ser Thr Arg Ile Pro Lys Val Gln Lys Leu Leu Gln Asp
            340                 345                 350

Phe Phe Asn Gly Arg Asp Leu Asn Lys Ser Ile Asn Pro Asp Glu Ala
            355                 360                 365

Val Ala Tyr Gly Ala Ala Val Gln Ala Ala Ile Leu Met Gly Asp Lys
            370                 375                 380

Ser Glu Asn Val Gln Asp Leu Leu Leu Asp Val Ala Pro Leu Ser
385                 390                 395                 400

Leu Gly Leu Glu Thr Ala Gly Gly Val Met Thr Ala Leu Ile Lys Arg
                405                 410                 415

Asn Ser Thr Ile Pro Thr Lys Gln Thr Gln Ile Phe Thr Thr Tyr Ser
                420                 425                 430

Asp Asn Gln Pro Gly Val Leu Ile Gln Val Tyr Glu Gly Glu Arg Ala
            435                 440                 445

Met Thr Lys Asp Asn Asn Leu Leu Gly Arg Phe Glu Leu Ser Gly Ile
450                 455                 460

Pro Pro Ala Pro Arg Gly Val Pro Gln Ile Glu Val Thr Phe Asp Ile
465                 470                 475                 480

Asp Ala Asn Gly Ile Leu Asn Val Thr Ala Thr Asp Lys Ser Thr Gly
                485                 490                 495

Lys Ala Asn Lys Ile Thr Ile Thr Asn Asp Lys Gly Arg Leu Ser Lys
                500                 505                 510

Glu Glu Ile Glu Arg Met Val Gln Glu Ala Glu Lys Tyr Lys Ala Glu
            515                 520                 525

Asp Glu Val Gln Arg Glu Arg Val Ser Ala Lys Asn Ala Leu Glu Ser
530                 535                 540

Tyr Ala Phe Asn Met Lys Ser Ala Val Glu Asp Glu Gly Leu Lys Gly
545                 550                 555                 560

Lys Ile Ser Glu Ala Asp Lys Lys Val Leu Asp Lys Cys Gln Glu
                565                 570                 575

Val Ile Ser Trp Leu Asp Ala Asn Thr Leu Ala Glu Lys Asp Glu Phe
            580                 585                 590

Glu His Lys Arg Lys Glu Leu Glu Gln Val Cys Asn Pro Ile Ile Ser
            595                 600                 605

Gly Leu Tyr Gln Gly Ala Gly Gly Pro Gly Pro Gly Gly Phe Gly Ala
610                 615                 620

Gln Gly Pro Lys Gly Gly Ser Gly Ser Gly Pro Pro Ile Glu Glu Val
625                 630                 635                 640

Asp

<210> SEQ ID NO 17
<211> LENGTH: 9
<212> TYPE: PRT
<213> ORGANISM: Homo sapiens

<400> SEQUENCE: 17

Thr Tyr Gly Pro Val Phe Met Cys Leu
1               5

<210> SEQ ID NO 18
<211> LENGTH: 9
```

```
<212> TYPE: PRT
<213> ORGANISM: Homo sapiens

<400> SEQUENCE: 18

Arg Tyr Leu Arg Asp Gln Gln Leu Leu
1               5

<210> SEQ ID NO 19
<211> LENGTH: 9
<212> TYPE: PRT
<213> ORGANISM: Homo sapiens

<400> SEQUENCE: 19

Gly Ile Leu Gly Phe Val Phe Thr Leu
1               5

<210> SEQ ID NO 20
<211> LENGTH: 9
<212> TYPE: PRT
<213> ORGANISM: Homo sapiens

<400> SEQUENCE: 20

Ser Leu Tyr Asn Thr Val Ala Thr Leu
1               5

<210> SEQ ID NO 21
<211> LENGTH: 9
<212> TYPE: PRT
<213> ORGANISM: Homo sapiens

<400> SEQUENCE: 21

Leu Thr Ala Gly Phe Leu Ile Phe Leu
1               5

<210> SEQ ID NO 22
<211> LENGTH: 9
<212> TYPE: PRT
<213> ORGANISM: Homo sapiens

<400> SEQUENCE: 22

Ala Thr Leu Glu Glu Met Met Thr Ala
1               5
```